United States Patent
Hur et al.

(10) Patent No.: US 9,527,744 B2
(45) Date of Patent: Dec. 27, 2016

(54) METHOD FOR MANUFACTURING REDUCED GRAPHENE OXIDE USING SOLID HYDRAZINE DERIVATIVE

(71) Applicant: SOGANG UNIVERSITY RESEARCH FOUNDATION, Seoul (KR)

(72) Inventors: Nam Hwi Hur, Seoul (KR); Byeongno Lee, Yongin-si (KR); Kyu Hyung Lee, Seoul (KR)

(73) Assignee: SOGANG UNIVERSITY RESEARCH FOUNDATION, Seoul (KR)

( * ) Notice: Subject to any disclaimer, the term of this patent is extended or adjusted under 35 U.S.C. 154(b) by 77 days.

(21) Appl. No.: 14/438,000

(22) PCT Filed: Nov. 14, 2013

(86) PCT No.: PCT/KR2013/010349
§ 371 (c)(1),
(2) Date: Aug. 18, 2015

(87) PCT Pub. No.: WO2014/077602
PCT Pub. Date: May 22, 2014

(65) Prior Publication Data
US 2015/0344311 A1 Dec. 3, 2015

(30) Foreign Application Priority Data
Nov. 14, 2012 (KR) .......................... 10-2012-0128862

(51) Int. Cl.
*C01B 31/04* (2006.01)
*C07C 243/10* (2006.01)
*B82Y 40/00* (2011.01)

(52) U.S. Cl.
CPC ....... *C01B 31/0446* (2013.01); *C01B 31/0438* (2013.01); *C07C 243/10* (2013.01); *B82Y 40/00* (2013.01); *Y10S 977/734* (2013.01); *Y10S 977/842* (2013.01)

(58) Field of Classification Search
CPC ............... C07C 243/10; C01B 31/0438; C01B 31/0446; C01B 31/04; C01B 31/0407; C01B 31/0415; C01B 2204/00; C01B 2204/02; C01B 2204/04; C01B 2204/06; C01B 2204/065; C01B 2204/20; B82Y 40/00; Y10S 977/734; Y10S 977/842
USPC ................................................... 423/448, 460
See application file for complete search history.

(56) References Cited

FOREIGN PATENT DOCUMENTS

| KR | 1020110110067 A | 10/2011 |
| KR | 101093140 B1 | 12/2011 |
| KR | 10-2012-0039799 A | 4/2012 |
| KR | 1020120073996 A | 7/2012 |
| KR | 1020120114112 A | 10/2012 |

OTHER PUBLICATIONS

Stankovich, et al., Synthesis of graphene-based nanosheets via chemical reduction of exfoliated graphite oxide, Carbon 2007; 45: 1558-1565.*
Park, et al., Hydrazine-reduction of graphite- and graphene oxide, Carbon 2011; 49: 3019-3023.*
Gao, et al., Hydrazine and Thermal Reduction of Graphene Oxide: Reaction Mechanisms, Production Structures, and Reaction Design, J. Phys. Chem. C 2010; 114: 832-842.*
Dreyer, et al., The chemistry of graphene oxide, Chem. Soc. Rev. 2010; 39: 228-240.*
Lee, et al., Large scale production of highly conductive reduced graphene oxide sheets by a solvent-free low temperature reduction, Carbon 2014; 69: 327-335.*
International Search Report from International Application No. PCT/KR2013/010349 mailed Jan. 28, 2014.

* cited by examiner

*Primary Examiner* — Daniel C McCracken
(74) *Attorney, Agent, or Firm* — Brundidge & Stanger, P.C.

(57) ABSTRACT

The present invention relates to a method for preparing reduced graphene oxide from graphene oxide using a solid hydrazine derivative.

13 Claims, 9 Drawing Sheets

METHOD FOR MANUFACTURING REDUCED GRAPHENE OXIDE USING SOLID HYDRAZINE DERIVATIVE

TECHNICAL FIELD

The present invention relates to a method for preparing reduced graphene oxide from graphene oxide using a solid hydrazine derivative.

BACKGROUND

Graphene purely consists of carbon and has an aligned hexagonal structure formed into a honeycomb shape similar to graphite. However, graphene is formed of a monoatomic layer and thus basically has a big difference in physical property from graphite having a layered structure formed by layering numerous sheets of graphene. Unlike graphite, graphene behaves like Dirac fermions with a zero effective mass and is transparent enough to transmit more than 98% of light; it is about 200 times stronger than steel, two or more times higher in thermal conductivity than diamond, higher in electrical conductivity than copper, and higher in charge carrier mobility than silicon. Graphene has been expected to be widely applied to flexible displays, transparent electrodes, solar cells, etc. due to its excellent optical, mechanical, and electrical properties. Therefore, a lot of studies on the method for mass-producing graphene, the method for improving electrical conductivity, etc. have been conducted.

Various methods for preparing monolayer graphene or multilayer graphene including multiple layers have been reported. Particularly, a mechanical method of mechanically separating graphene from graphite, a chemical vapor deposition method of directly synthesizing graphene on a substrate, and a chemical method of oxidizing graphite to produce graphene oxide and preparing reduced graphene oxide from the produced graphene oxide have attracted a lot of attention and have been studied. The mechanical method has an advantage in that it can obtain undamaged monolayer graphene, but has a disadvantage in that it is not suitable for mass production. The chemical vapor deposition method has advantages in that it is suitable for mass production and can obtain a relatively high-quality multilayer graphene thin film, but has a disadvantage in that graphene is grown only on a specific metal used as a catalyst and the grown graphene needs to be transferred to another substrate. However, in the chemical method, graphite is oxidized in an acidic solution with addition of a strong oxidizer such as $KMnO_4$ or $H_2O_2$ to produce graphene oxide containing oxygen, and then, reduced graphene oxide is prepared through a solution process of adding a reducing agent such as hydrazine ($NH_2NH_2$) or $NaBH_4$ or a heat treatment in a vacuum or in a hydrogen atmosphere. The chemical method is relatively easily performed and economical, and, thus, can produce reduced graphene oxide which can be applied in various ways. However, the chemical method has a disadvantage in that graphene loses its own optical and electrical properties due to defects and nitrogen doping, etc., and, thus, cannot exhibit all of its properties. Nonetheless, studies on the process for preparing reduced graphene oxide have been continuously conducted. This is because reduced graphene oxide has enough properties to be applied to various fields such as electrodes, conductive inks, catalyst supports, etc.

Among various methods for preparing a reduced graphene oxide, particularly, a method using a liquid hydrazine is suitable for mass production and enables a graphene surface to be easily functionalized and also readily produces relatively high-purity graphene without metallic impurities. Thus, it is one of the most widely used methods (Korean Patent Laid-open Publication No. 10-2012-0039799). However, the reduced graphene oxide prepared using liquid hydrazine has a low carbon-oxygen atomic ratio of about 10 due to water contained during the process and also has a low conductivity due to a high content of nitrogen. Until now, the chemical reduction methods using hydrazine includes a solution process using a solvent containing water, and, thus, an additional dehydrating and solvent-removing process such as a high-temperature heat treatment are required. Due to that a small amount of moisture remains in the reduced graphene oxide despite of such an additional process, its durability is decreased and also, its conductivity becomes lower than that of graphene.

DETAILED DESCRIPTION OF THE INVENTION

Problems to be Solved by the Invention

In view of the foregoing problems, one purpose of the present disclosure is to provide a method for preparing a high-conductivity reduced graphene oxide from graphene oxide using a stable and highly reactive solid hydrazine derivative in a dry condition without moisture.

However, problems to be solved by the present disclosure are not limited to the above-described problems. Although not described herein, other problems to be solved by the present disclosure can be clearly understood by those skilled in the art from the following descriptions.

Means for Solving the Problems

In one aspect of the present disclosure, there is provided a method for preparing a reduced graphene oxide, including: reducing a graphene oxide using, as a reducing agent, a solid hydrazine derivative compound represented by the following Chemical Formula II or Chemical Formula III that is generated from a reaction between a hydrazine represented by the following Chemical Formula I or its derivative with carbon dioxide:

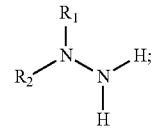

[Chemical Formula I]

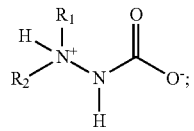

[Chemical Formula II]

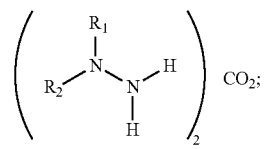

[Chemical Formula III]

wherein in Chemical Formulas I, II and III,
each of $R_1$ and $R_2$ is independently hydrogen; or, a member selected from the group consisting of an aliphatic hydrocarbon group of 1 to 30 carbons, a substitutable aliphatic hydrocarbon group of 1 to 30 carbons, a substitutable aliphatic cyclic group of 3 to 30 carbons, an aliphatic heterocyclic group of 3 to 30 carbons, an aromatic cyclic group of 6 to 30 carbons, and an aromatic heterocyclic group of 6 to 30 carbons; or, a member selected from the group consisting of an aliphatic hydrocarbon group of 1 to 30 carbons including at least one of Si, O, S, Se, N, P, or As, an aliphatic cyclic group of 3 to 30 carbons including at least one of Si, O, S, Se, N, P, or As, an aliphatic heterocyclic group of 3 to 30 carbons including at least one of Si, O, S, Se, N, P, or As, and an aromatic heterocyclic group of 6 to 30 carbons including at least one of Si, O, S, Se, N, P, or As.

Effect of the Invention

According to the present disclosure, the reduced graphene oxide that is prepared via solid-phase reaction by reacting graphene oxide with a stable and highly reactive solid hydrazine derivative in a dry condition without moisture contains a very small amount of impurity, has a high conductivity, and contains almost no moisture, resulting in an effect of minimizing deterioration in a physical property caused by moisture. Further, there is provided an additional effect in that a process for synthesizing reduced graphene oxide is very simple and it is a highly eco-friendly without producing environmental pollutants and highly economical process.

In the method for preparing reduced graphene oxide according to the present disclosure, graphene oxide powder and solid hydrazine derivative powder are subject to a solid-phase reaction by grinding those without using a solvent to prepare reduced graphene oxide. Therefore, an additional separation process is not needed, and reduced graphene oxide having a high purity and high conductivity can be prepared.

BEST MODE FOR CARRYING OUT THE INVENTION

Figure 1A:
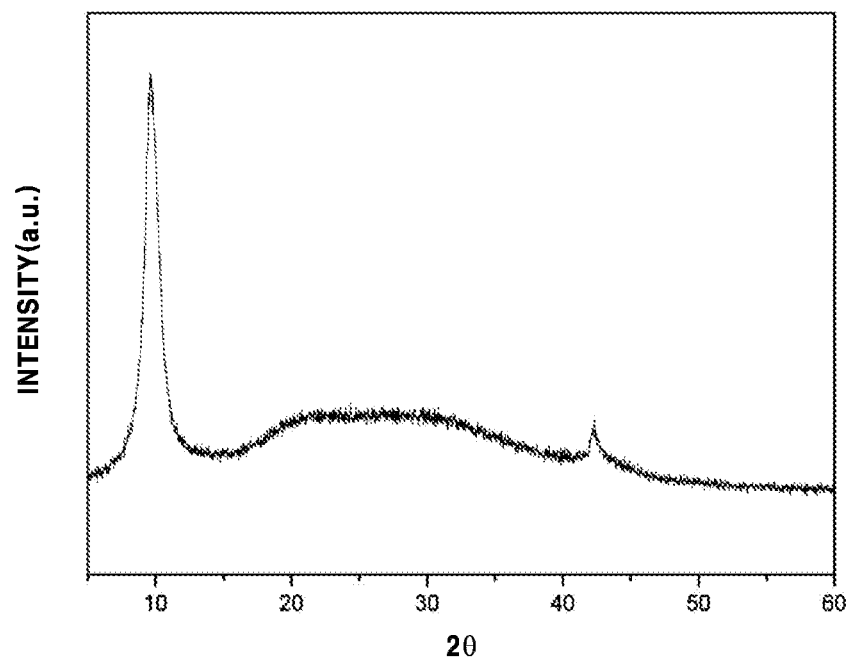
FIG. 1A shows an XRD (X-ray diffraction) spectrum of graphene oxide in accordance with an example of the present disclosure.
Figure 1B:
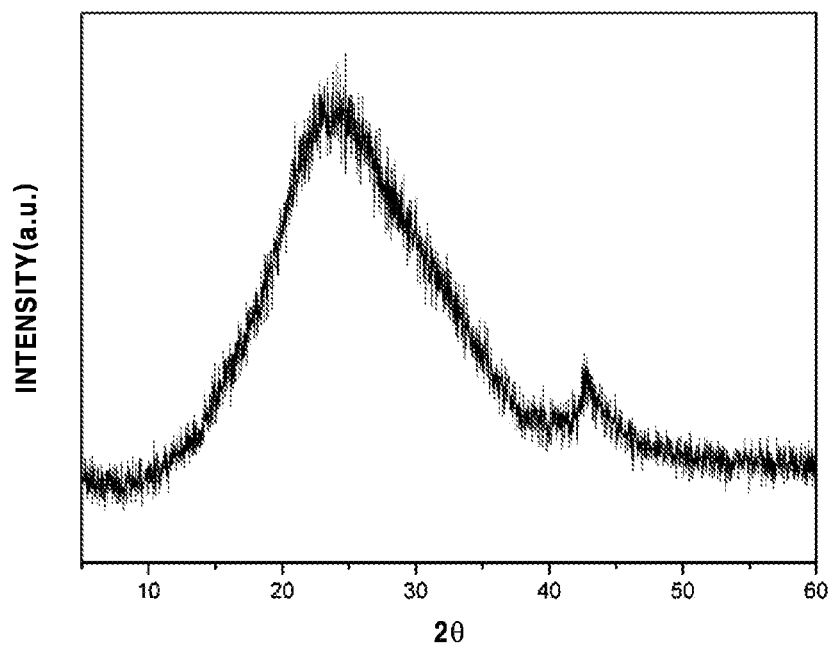
FIG. 1B shows an XRD (X-ray diffraction) spectrum of reduced graphene oxide in accordance with an example of the present disclosure.
Figure 2:
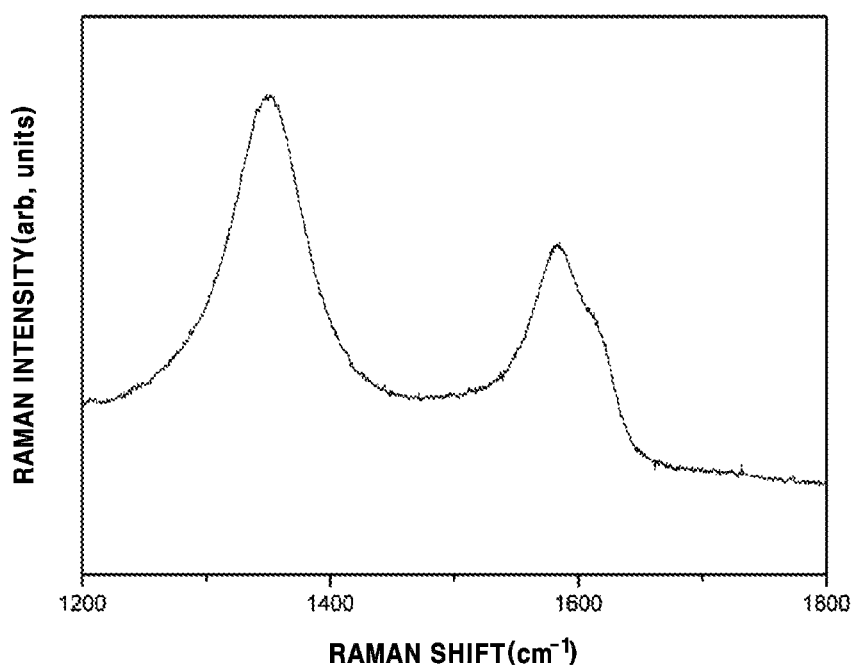
FIG. 2 shows a Raman spectrum of reduced graphene oxide in accordance with an example of the present disclosure.
Figure 3:
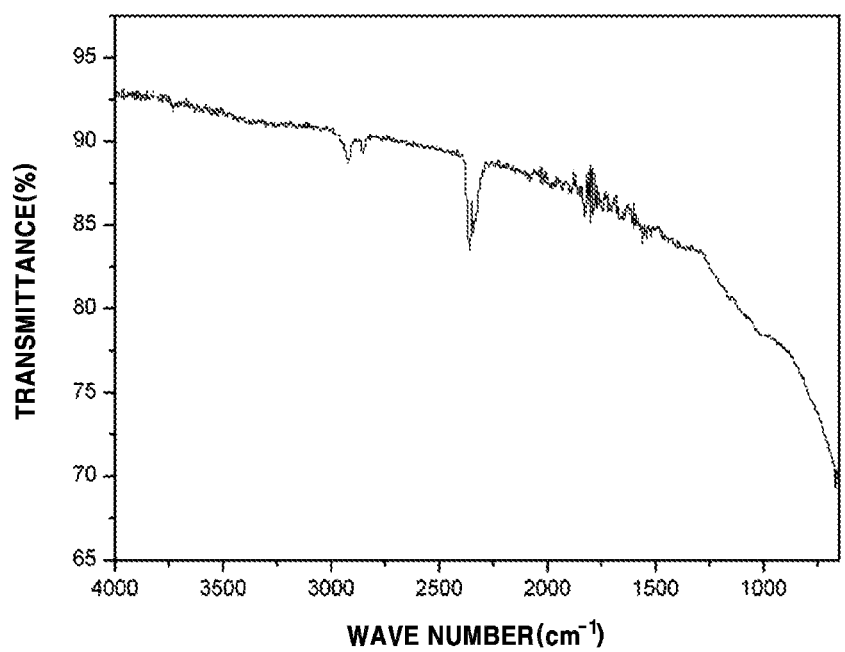
FIG. 3 shows an IR (infra-red spectroscopy) spectrum of reduced graphene oxide in accordance with an example of the present disclosure. Herein, a peak at a wave number of around 2300 is a peak of carbon dioxide.
Figure 4:
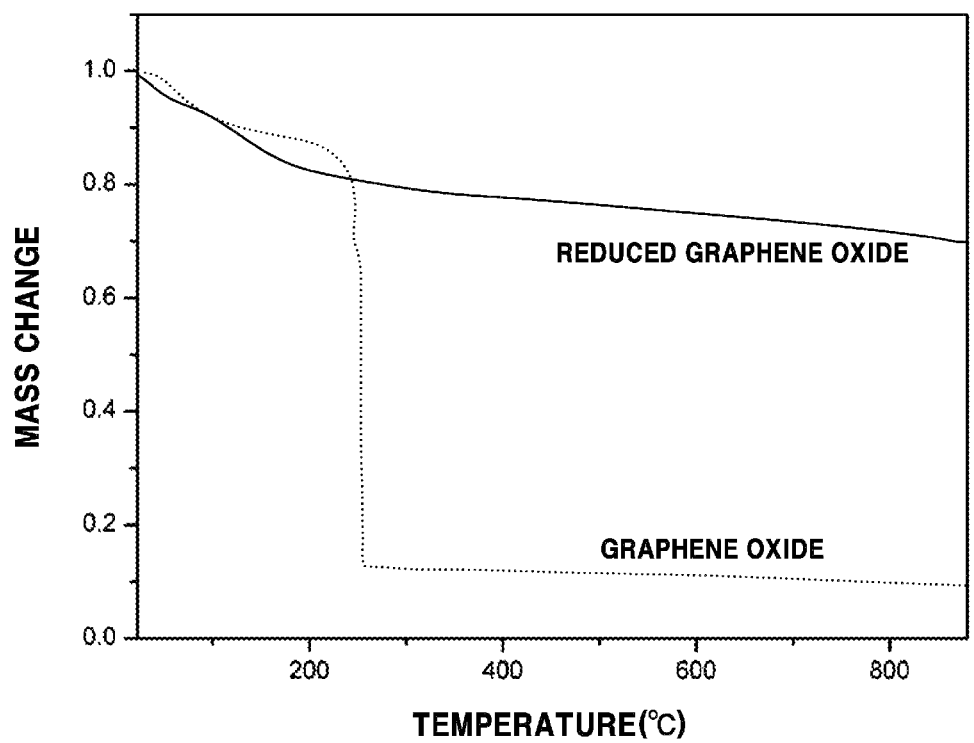
FIG. 4 shows TGA (thermogravimetric analysis) data of graphene oxide and reduced graphene oxide in accordance with an example of the present disclosure.
Figure 5:
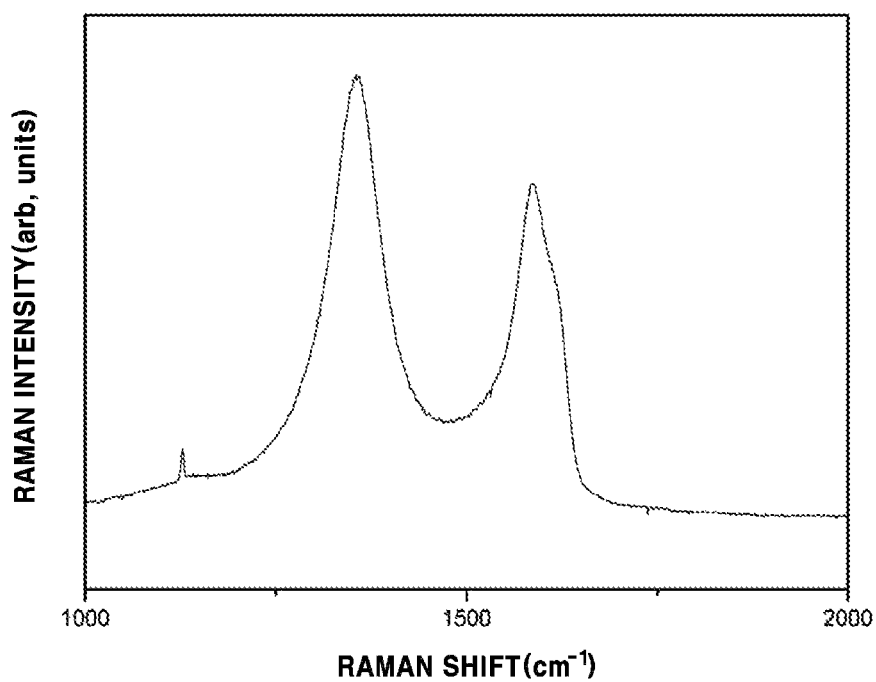
FIG. 5 shows a Raman spectrum of reduced graphene oxide in accordance with an example of the present disclosure.
Figure 6:
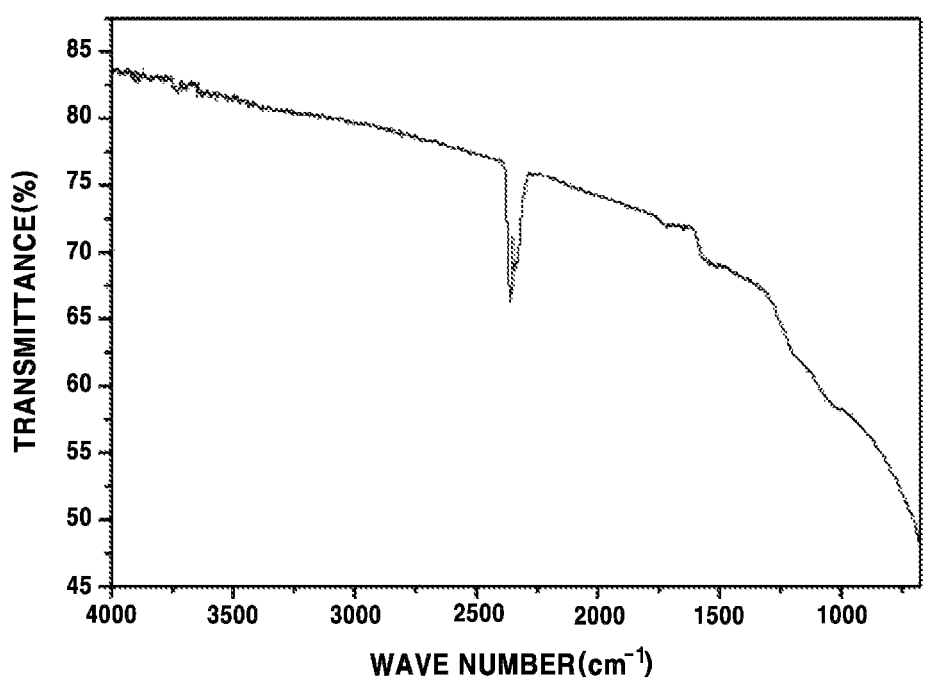
FIG. 6 shows an IR spectrum of reduced graphene oxide in accordance with an example of the present disclosure. Herein, a peak at a wave number of around 2300 is a peak of carbon dioxide.
Figure 7:
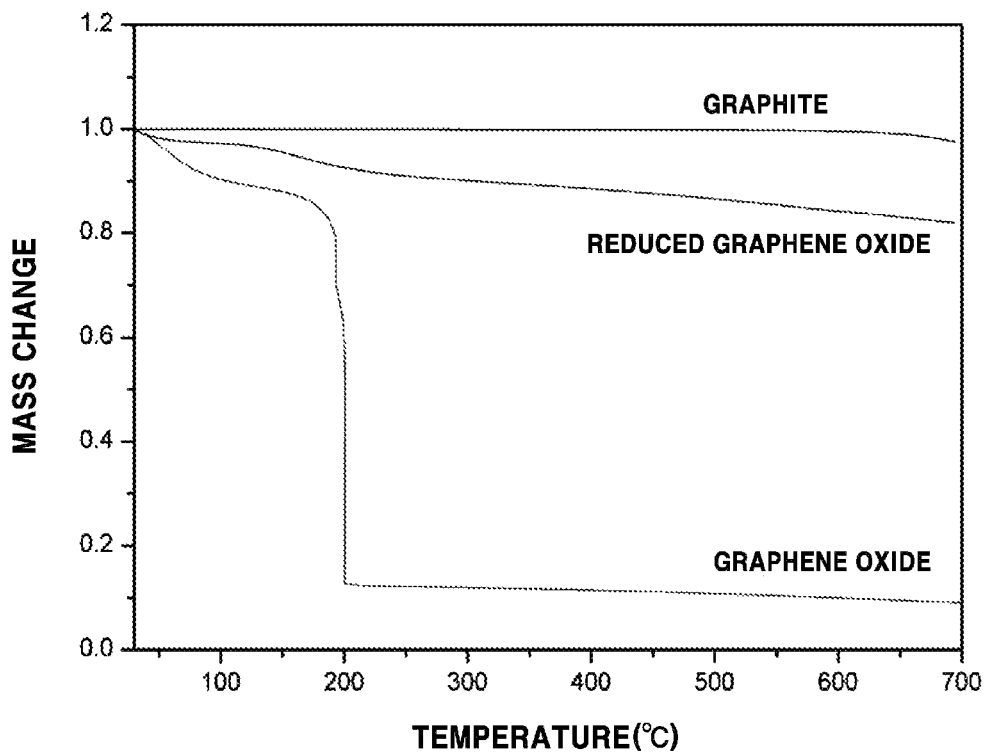
FIG. 7 shows TGA data of graphene oxide, reduced graphene oxide, and graphite in accordance with an example of the present disclosure.
Figure 8:
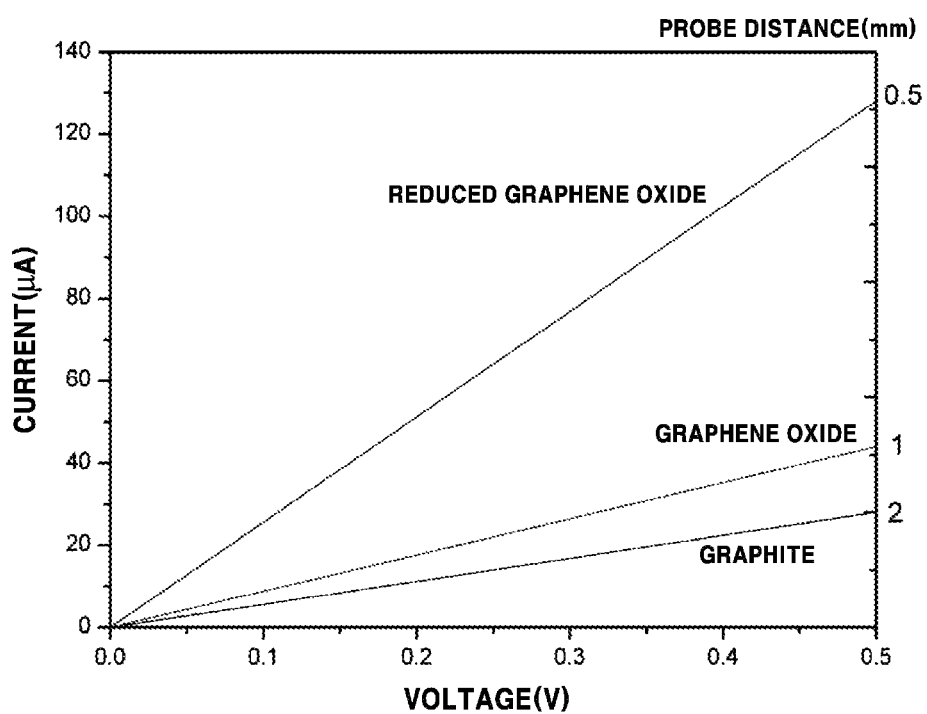
FIG. 8 shows an I/V (current/voltage) curve of reduced graphene oxide in accordance with an example of the present disclosure.
Figure 9:
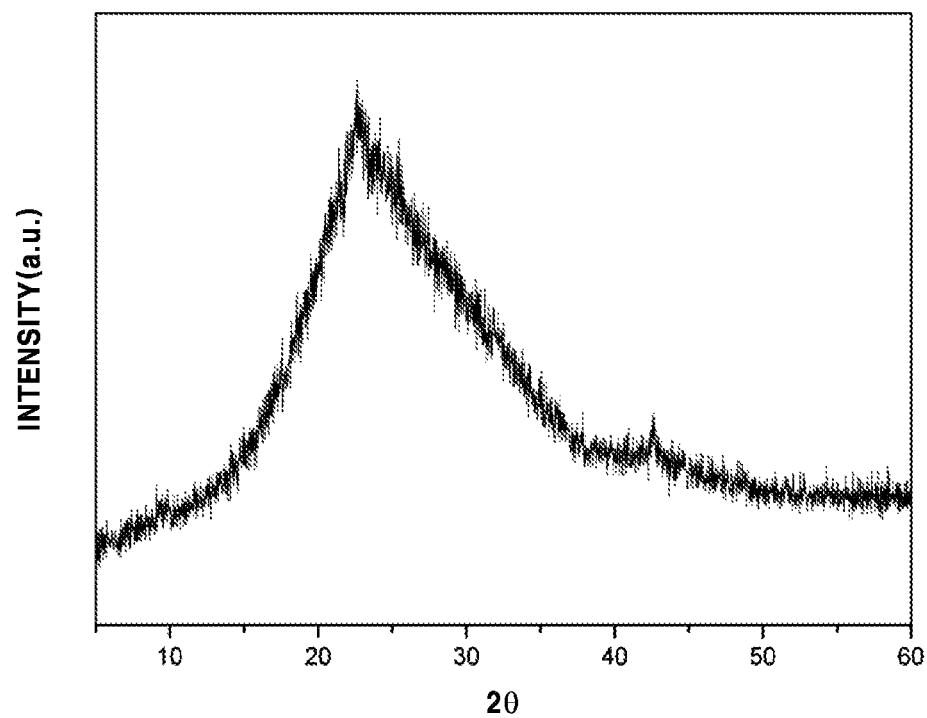
FIG. 9 shows an XRD spectrum of reduced graphene oxide in accordance with an example of the present disclosure.

Hereinafter, embodiments of the present disclosure will be described in detail with reference to the accompanying drawings so that the present disclosure may be readily implemented by those skilled in the art. However, it is to be noted that the present disclosure is not limited to the embodiments but can be embodied in various other ways. In drawings, parts irrelevant to the description are omitted for the simplicity of explanation, and like reference numerals denote like parts through the whole document of the present disclosure.

Through the whole document of the present disclosure, the term "connected to" or "coupled to" that is used to designate a connection or coupling of one element to another element includes both a case that an element is "directly connected or coupled to" another element and a case that an element is "electronically connected or coupled to" another element via still another element.

Through the whole document of the present disclosure, the term "on" that is used to designate a position of one element with respect to another element includes both a case that the one element is adjacent to the another element and a case that any other element exists between these two elements.

Through the whole document of the present disclosure, the term "comprises or includes" and/or "comprising or including" used in the document means that one or more other components, steps, operation and/or existence or addition of elements are not excluded in addition to the described components, steps, operation and/or elements unless context dictates otherwise. The term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document of the present disclosure, the term "combinations of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document of the present disclosure, the term "an alkyl" means a straight- or branched, non-substituted or substituted saturated hydrocarbon group having 1 to 30 carbons, for example, 1 to 20, 1 to 10, or 1 to 5 carbons, and may include, for example, methyl, ethyl, propyl, isopropyl, isobutyl, sec butyl, tert butyl, pentyl, hexyl, heptyl, octyl, nonyl, decyl, undecyl, tridecyl, pentadecyl, heptadecyl, and the like. $C_1$-$C_{10}$ alkyl means an alkyl group having an alkyl unit of 1 to 10 carbons, and does not include the number of carbons of a substituent when the $C_1$-$C_{10}$ alkyl is substituted.

Through the whole document of the present disclosure, the term "an aliphatic hydrocarbon" may be saturated or unsaturated aliphatic hydrocarbon, and may include, for example, but not limited to, an alkyl, an alkenyl, an alkynyl, and the like.

Through the whole document of the present disclosure, the term "an alkenyl" means a straight- or branched non-substituted or substituted unsaturated hydrocarbon group having a designated number of carbons, for example, 2 to 30, 2 to 20, 2 to 10, or 2 to 5 carbons, and may include, for example, but not limited to, ethenyl, vinyl, propenyl, allyl, isopropenyl, butenyl, isobutenyl, t-butenyl, n-pentenyl and n-hexenyl.

Through the whole document of the present disclosure, the term "an aromatic cycle or substituted aromatic heterocycle" may include, for example, but not limited to, an aryl compound, hetero aryl, aryl alkyl, a fused aryl group, and the like.

Through the whole document of the present disclosure, the term "an aryl" means an overall or partially unsaturated, substituted or non-substituted monocyclic or polycyclic carbocycle. $C_6$-$C_{30}$ aryl means an aryl group having a carbocyclic atom of 6 to 30 carbons, and does not include the number of carbons of a substituent when the $C_6$-$C_{30}$ aryl is substituted. Desirably, an aryl is monoaryl or biaryl. The monoaryl desirably has 5 to 6 carbons, and the biaryl desirably has 9 to 10 carbons. Most desirably, the aryl is substituted or non-substituted phenyl. When the monoaryl, e.g., phenyl is substituted, the substitution may occur at various positions by various substituents, e.g., a halo, hydroxy, nitro, cyano, or a $C_1$-$C_4$ substituted or non-substituted straight- or branched-chain alkyl or a $C_1$-$C_4$ straight- or branched-chain alkoxy group.

Through the whole document of the present disclosure, the term "a heteroaryl" is a heterocyclic aromatic group, and may include Si, O, S, Se, N, P or As as a hetero atom. $C_3$-$C_{30}$ heteroaryl means a heteroaryl group having a carbocyclic atom of 3 to 30 carbons, and does not include the number of carbons of a substituent when the $C_3$-$C_{30}$ heteroaryl is substituted. The number of the hetero atoms is preferably 1 to 2. In the heteroaryl, aryl is desirably monoaryl or biaryl, and most desirably, monoaryl. The heteroaryl may be substituted at various positions by various substituents, e.g., a halo, hydroxy, nitro, cyano, or a $C_1$-$C_4$ substituted or non-substituted straight- or branched-chain alkyl, or a $C_1$-$C_4$ straight- or branched-chain alkoxy group.

Through the whole document of the present disclosure, the term "an arylalkyl" means an alkyl group substituted with an aryl group. $C_6$-$C_{30}$ arylalkyl means arylalkyl having an arylalkyl unit having 6 to 30 carbons, and does not include the number of carbons of a substituent when the $C_6$-$C_{30}$ arylalkyl is substituted. In the arylalkyl, aryl is desirably monoaryl or biaryl, and alkyl is desirably $C_1$-$C_3$ alkyl, and more desirably, $C_1$ alkyl. In the arylalkyl, aryl may be substituted at various positions by various substituents, e.g., a halo, hydroxy, nitro, cyano, or a $C_1$-$C_4$ substituted or non-substituted straight- or branched-chain alkyl, a $C_1$-$C_4$ straight- or branched-chain alkoxy or alkylcarboxylnitro group.

Through the whole document of the present disclosure, the term "a fused aryl group" means a cyclic form consisting of fused multiple aryl rings, and may include naphthalene, phenanthrene, anthracene, benzo[a]pyrene, benzo[b]pyrene, benzo[e]pyrene, acenaphthalene, acenaphthene, benzo[b]fluoranthene, benzo[j]fluroranthene, chrysene, fluoranthene, fluorene, pyrene, and the like, which are substituted or non-substituted fused aryl groups. The fused aryl group may be substituted at various positions by various substituents, e.g., a halo, hydroxy, nitro, cyano, or a $C_1$-$C_4$ substituted or non-substituted straight- or branched-chain alkyl, or a $C_1$-$C_4$ straight- or branched-chain alkoxy group.

Hereinafter, the present disclosure will be described in detail using exemplary embodiments and examples with reference to the accompanied drawings. However, the present disclosure is not limited to the following embodiments and examples.

In a first aspect of the present disclosure, there is provided a method for preparing a reduced graphene oxide, including reducing a graphene oxide using, as a reducing agent, a solid hydrazine derivative compounds represented by the following Chemical Formula II or Chemical Formula III that is generated from a reaction between a hydrazine represented by the following Chemical Formula I or its derivative with carbon dioxide:

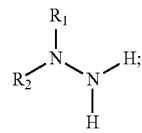

[Chemical Formula I]

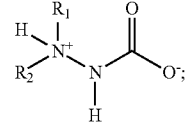

[Chemical Formula II]

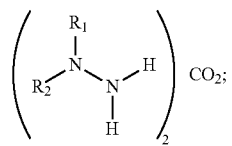

[Chemical Formula III]

In Chemical Formulas I, II and III,
each of $R_1$ and $R_2$ is independently hydrogen; or, a member selected from the group consisting of an aliphatic hydrocarbon group of 1 to 30 carbons, a substitutable aliphatic hydrocarbon group of 1 to 30 carbons, a substitutable aliphatic cyclic group of 3 to 30 carbons, an aliphatic heterocyclic group of 3 to 30 carbons, an aromatic cyclic group of 6 to 30 carbons, and an aromatic heterocyclic group of 6 to 30 carbons; or, a member selected from the group consisting of an aliphatic hydrocarbon group of 1 to 30 carbons including at least one of Si, O, S, Se, N, P, or As, an aliphatic cyclic group of 3 to 30 carbons including at least one of Si, O, S, Se, N, P, or As, an aliphatic heterocyclic group of 3 to 30 carbons including at least one of Si, O, S, Se, N, P, or As, and an aromatic heterocyclic group of 6 to 30 carbons including at least one of Si, O, S, Se, N, P, or As.

In an embodiment of the present disclosure, each of the $R_1$ and $R_2$ is independently hydrogen; or a member selected from the group consisting of an aliphatic hydrocarbon group or substituted aliphatic hydrocarbon group of 1 to 30 carbons, for example, 1 to 25, 1 to 20, 1 to 15, or 1 to 10 carbons, and a substituted aliphatic cyclic group, aliphatic heterocyclic group, aromatic cyclic group, and aromatic heterocyclic group of 3 to 30 carbons, for example, 3 to 25, 3 to 20, 3 to 15, or 3 to 10 carbons; or, a member selected from the group consisting of an aliphatic hydrocarbon group and aliphatic cyclic group of 1 to 30 carbons, for example, 1 to 25, 1 to 20, 1 to 15, and 1 to 10 carbons, including at least one of Si, O, S, Se, N, P or As, and an aliphatic heterocyclic group and aromatic heterocyclic group of 3 to 30 carbons, for example, 3 to 25, 3 to 20, 3 to 15, or 3 to 10 carbons, including at least one of Si, O, S, Se, N, P, or As, but may not be limited thereto.

In an embodiment of the present disclosure, for a quantitative (1:1) reaction of hydrazine or its derivatives with carbon dioxide, a compound represented by the following Chemical Formula I is reacted with high-pressure carbon dioxide, so that hydrazine or its derivative compound, to which carbon dioxide is chemically bonded and which is represented by the following Chemical Formula II, can be synthesized. The synthesized compound of Chemical Formula II can be converted into Chemical Formula III at a proper temperature depending on a substituent as shown in Reaction Formula 1. Chemical Formulas I, II and III may have the following structures:

In an embodiment of the present disclosure, the solid hydrazine derivative represented by Chemical Formulas II and III can be obtained under a solvent-free condition or under water, an alcohol of $C_1$-$C_{12}$, an ether of $C_2$-$C_{12}$, or a mixed solvent thereof. Especially, when the reaction is accomplished under an alcohol solvent of $C_1$-$C_{12}$, a hydrazine carboxylic acid or a derivative thereof having a high purity can be obtained.

When an alcohol is used as a solvent, the solvent may include methanol, ethanol, propanol, isopropanol, n-butanol, isobutanol, sec-butanol, tert-butanol, n-pentanol, isopentanol, sec-pentanol, tert-pentanol, hexanol, heptanol, octanol, nonanol, decanol, undecanol, dodecanol, pentadecanol, and the like, but may not be limited thereto. The solvent may include a polyol such as ethyleneglycol, glycerol, erythritol, xylitol, or mannitol, but may not be limited thereto.

When an ether is used as a solvent, the solvent may include dimethylether, diethylether, THF, dioxin, and the like, but may not be limited thereto.

In an embodiment of the present disclosure, for the carbon dioxide, not only vapor or liquid carbon dioxide but also carbon dioxide in a supercritical state or a solid-state dry ice may be used, but may not be limited thereto.

In an embodiment of the present disclosure, the solid hydrazine derivative represented by Chemical Formulas II and III may be prepared under a high-pressure condition. After the reaction under the high-pressure condition, the pressure may be reduced to from about 0.01 MPa to about 0.1 MPa to evaporate excess carbon dioxide, but may not be limited thereto.

In an embodiment of the present disclosure, the reducing the graphene oxide may be performed without using a solvent, but may not be limited thereto.

In an embodiment of the present disclosure, the reducing the graphene oxide may include mixing the solid hydrazine derivative compound with the graphene oxide by grinding or milling those so as to be reacted in a solid state, but may not be limited thereto. The reducing the graphene oxide may be performed at about 80° C. or less, for example, from room temperature to about 80° C., from about 30° C. to about 80° C., from about 40° C. to about 80° C., from about 50° C. to about 80° C., from about 60° C. to about 80° C., from about 70° C. to about 80° C., from room temperature to about 70° C., from room temperature to about 60° C., from room temperature to about 50° C., or from room temperature to about 40° C., but may not be limited thereto. The reducing the graphene oxide may be performed for about from about

[Reaction Formula 1]

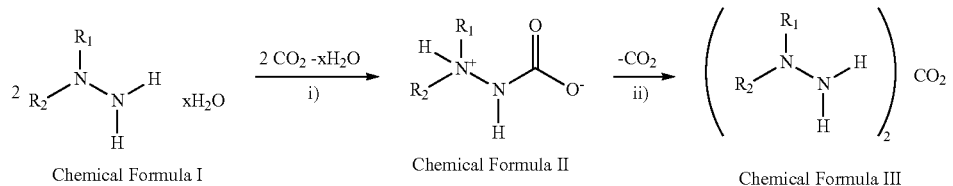

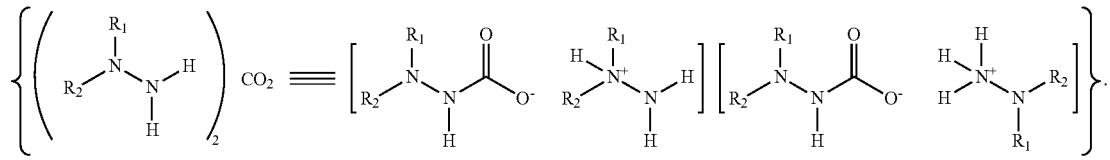

24 hours to about 60 hours, from about 30 hours to about 60 hours, from about 40 hours to about 60 hours, from about 50 hours to about 60 hours, from about 24 hours to about 50 hours, from about 24 hours to about 40 hours, or from about 24 hours to about 30 hours, but may not be limited thereto.

For example, when powder of the graphene oxide and powder of the solid hydrazine derivative are ground and mixed with each other in a mortar, the reduction reaction is slowly performed even at room temperature, so that reduced graphene oxide is produced. A reduction rate is very sharply increased when a reaction temperature is increased to about 80° C. According to the present disclosure, since the reduction can be performed in a solid state even at room temperature, the preparing process is simple and reduced graphene oxide having excellent properties can be mass-produced.

In an embodiment of the present disclosure, the reducing the graphene oxide may be performed by heating and sublimating the solid hydrazine derivative so as to be reacted with the graphene oxide, but may not be limited thereto. For example, while the graphene oxide is not in contact with the hydrazine derivative, the solid hydrazine derivative may be heated and sublimated at a temperature range of about 250° C. or less, for example, from about 30° C. to about 250° C., from about 50° C. to about 250° C., from about 100° C. to about 250° C., from about 150° C. to about 250° C., from about 200° C. to about 250° C., from about 30° C. to about 200° C., from about 30° C. to about 150° C., or from about 30° C. to about 100° C. to generate its vapor gas, and the vapor gas reduces the graphene oxide, but the present disclosure may not be limited thereto. The graphene oxide can be used in a form of a film or thin film, but may not be limited thereto.

In an embodiment of the present disclosure, the reducing the graphene oxide may be performed by reducing the solid hydrazine derivative compound and the graphene oxide in a slurry state in the presence of a non-aqueous solvent, but may not be limited thereto. The non-aqueous solvent may include solvents including an aliphatic hydrocarbon group of 1 to 30 carbons, a substitutable aliphatic hydrocarbon group of 1 to 30 carbons, a substitutable aliphatic cyclic group of 3 to 30 carbons, an aliphatic heterocyclic group of 3 to 30 carbons, an aromatic cyclic group of 6 to 30 carbons, an aromatic heterocyclic group of 6 to 30 carbons, an aliphatic hydrocarbon group of 1 to 30 carbons including at least one of Si, O, S, Se, N, P or As, an aliphatic cyclic group of 3 to 30 carbons including at least one of Si, O, S, Se, N, P or As, an aliphatic heterocyclic group of 3 to 30 carbons including at least one of Si, O, S, Se, N, P or As, an aromatic heterocyclic group of 6 to 30 carbons including at least one of Si, O, S, Se, N, P or As, an alcohol of $C_1$-$C_{12}$, and an ether of $C_2$-$C_{12}$, or mixed solvents thereof, but may not be limited thereto. After the reducing, the non-aqueous solvent may be removed by centrifugation, but may not be limited thereto.

The aliphatic hydrocarbon group may include an alkyl, an alkenyl group, and the like, but may not be limited thereto.

When an alcohol is used as the non-aqueous solvent, the alcohol solvent may include methanol, ethanol, propanol, isopropanol, n-butanol, isobutanol, sec-butanol, tert-butanol, n-pentanol, isopentanol, sec-pentanol, tert-pentanol, hexanol, heptanol, octanol, nonanol, decanol, undecanol, dodecanol, pentadecanol, and the like, but may not be limited thereto. The alcohol solvent may include a polyol such as ethyleneglycol, glycerol, erythritol, xylitol, and mannitol, but may not be limited thereto.

When an ether is used as the non-aqueous solvent, the ether may include dimethylether, diethylether, THF, dioxin, and the like, but may not be limited thereto.

In an embodiment of the present disclosure, a weight ratio of the solid hydrazine derivative with respect to the graphene oxide may be about 1:about 0.1 to about 5, but may not be limited thereto. By way of example, a weight ratio of the solid hydrazine derivative with respect to the graphene oxide may be about 1:about 0.1, about 1:about 0.5, about 1:about 1, about 1 about 2, about 1:about 3, about 1:about 4, or about 1:about 5, but may not be limited thereto.

In an embodiment of the present disclosure, the reducing the graphene oxide may be performed in a pressured-vessel using a gas having a pressure of from about 0.1 atm to about 500 atm, from about 1 atm to about 500 atm, from about 5 atm to about 500 atm, from about 10 atm to about 500 atm, from about 20 atm to about 500 atm, from about 50 atm to about 500 atm, from about 100 atm to about 500 atm, from about 200 atm to about 500 atm, from about 300 atm to about 500 atm, from about 0.1 atm to about 400 atm, from about 0.1 atm to about 300 atm, from about 0.1 atm to about 200 atm, from about 0.1 atm to about 100 atm, from about 0.1 atm to about 50 atm, or from about 0.1 atm to about 10 atm, but may not be limited thereto. The gas may include a member selected from the group consisting of oxygen, nitrogen, argon, hydrogen and combinations thereof, but may not be limited thereto.

In an embodiment of the present disclosure, if the solid hydrazine derivative is used as a reducing agent, the as-prepared reduced graphene oxide has a very high carbon to oxygen ratio of from about 15 to about 20 and a very high carbon to nitrogen ratio of from about 45 to about 55 and exhibits a very high electrical conductivity (<50 ohm). Reduced graphene oxide prepared by a conventional process using liquid hydrazine has a carbon to oxygen ratio of from about 8 to about 12 and a carbon to nitrogen ratio of from about 15 to about 25. Thus, it can be confirmed that the reduced graphene oxide according to the present disclosure has excellent properties.

Hereinafter, preferred examples of the present disclosure will be described. However, the following examples are provided only for understanding of the invention, but do not limit the present disclosure.

MODE FOR CARRYING OUT THE INVENTION

Example 1

Preparation of Reduced Graphene Oxide by Solid-Phase Reaction Between Hydrazinium Carboxylate as a Solid Hydrazine and Graphene Oxide Graphene oxide was prepared from graphite powder (Aldrich, <20 μm) by the modified Hummers' method using $H_2SO_4$ and $KMnO_4$ and then used. After 0.5 g of the graphene oxide and 0.2 g of hydrazinium carboxylate ($H_3N^+NHCO_2^-$) were ground in a mortar or ball mill, the mixed powder was put into a glass vial and the glass vial was filled with argon of atmospheric pressure and then kept at room temperature for 48 hours. The graphene oxide was converted into reduced graphene oxide according to the reaction time. After about 48 hours, all the graphene oxide was converted into reduced graphene oxide. Changes before and after the reaction were checked by XRD (X-ray diffraction), Raman, IR (infra-red spectroscopy), and TGA (thermogravimetric analysis). The results thereof were as shown in FIG. 1A to FIG. 4.

Results of Elemental Analysis:
1) Graphene oxide (GO): C, 54.86%; H, 2.17%; N, 0%
2) Reduced graphene oxide (RGO): C, 73.65%; H, 0.95%; N, 1.65%

Example 2

Preparation of Reduced Graphene Oxide by Solid-Phase Reaction Between Hydrazinium Carboxylate as a Solid Hydrazine and Graphene Oxide Example 2 was carried out in the same manner as Example 1 except a reaction temperature. Mixed powder of graphene oxide and hydrazinium carboxylate ($H_3N^+NHCO_2^-$) was kept in an oven at 80° C., instead of room temperature, for 30 minutes, so that reduced graphene oxide was obtained. Change before and after the reaction was checked by XRD, Raman, IR, TGA, and I/V (current/voltage) analysis. The results thereof were as shown in FIG. 5 to FIG. 9, which were identical with those of FIG. 1A to FIG. 4.

Results of Elemental Analysis:
1) Graphene oxide (GO): C, 54.86%; H, 2.17%; N, 0%
2) Reduced graphene oxide (RGO): C, 75.85%; H, 0.85%; N, 1.78%

Example 3

Figure 10:
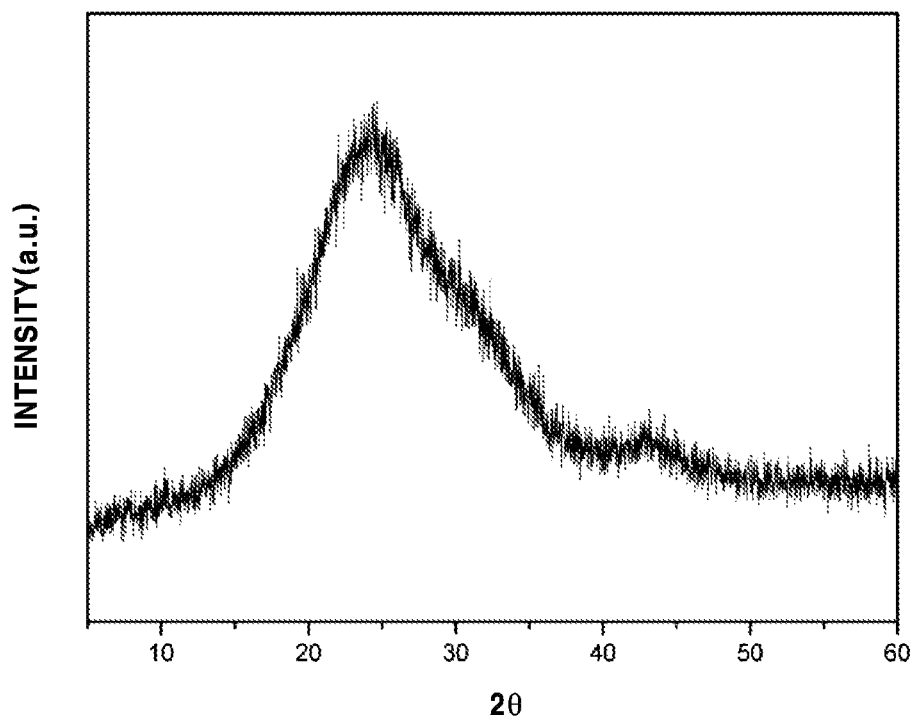
FIG. 10 shows an XRD spectrum of reduced graphene oxide in accordance with an example of the present disclosure.
Figure 11:
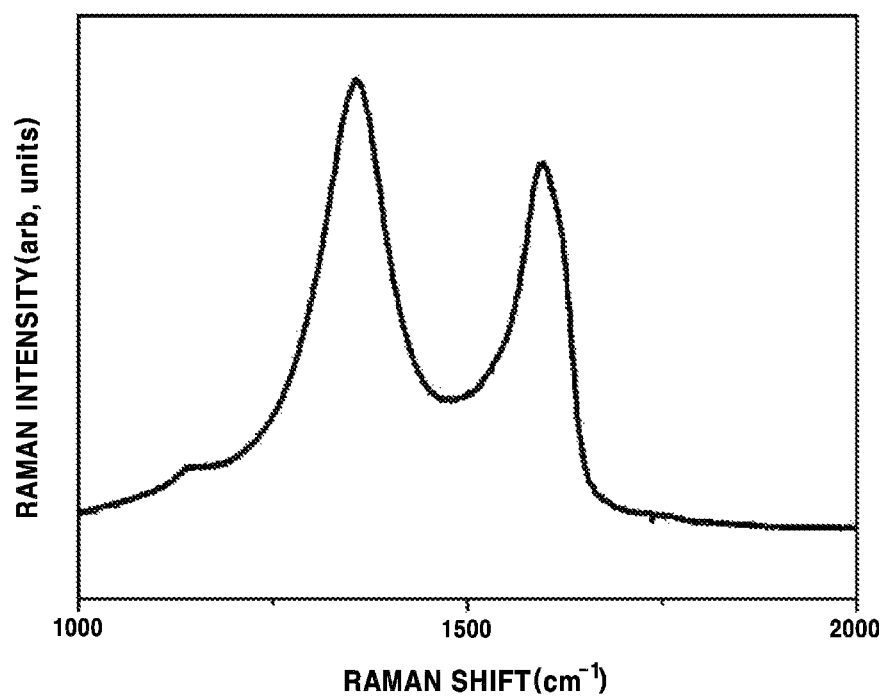
FIG. 11 shows a Raman spectrum of reduced graphene oxide in accordance with an example of the present disclosure.
Figure 12:
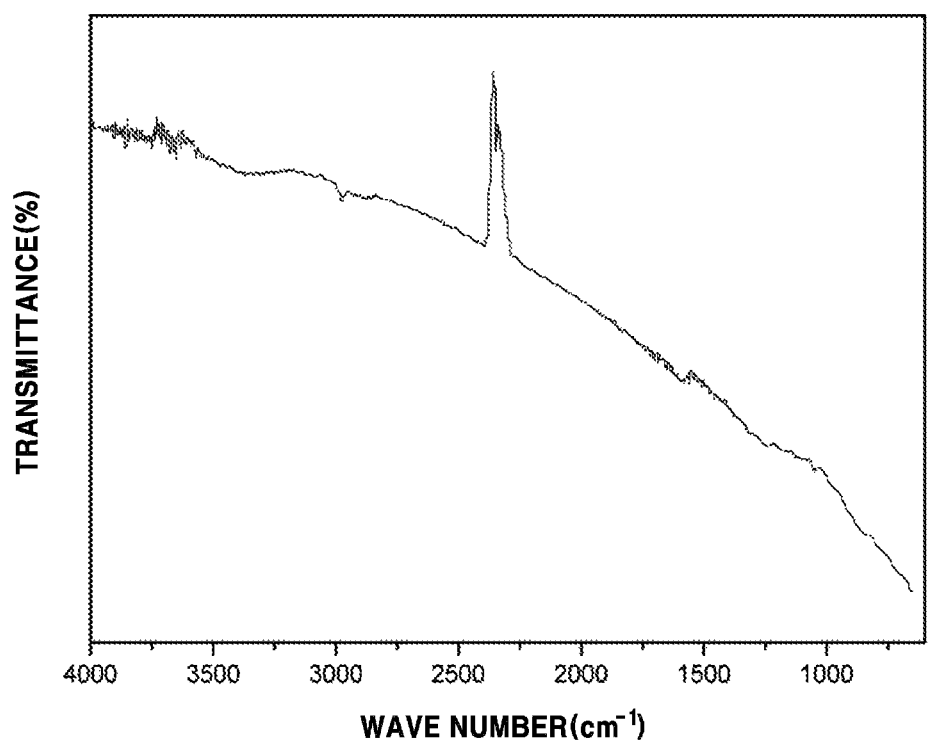
FIG. 12 shows an IR spectrum of reduced graphene oxide in accordance with an example of the present disclosure. Herein, a peak at a wave number of around 2300 is a peak of carbon dioxide.

Preparation of Reduced Graphene Oxide by Gas-Solid Reaction Between Hydrazinium Carboxylate as Solid Hydrazine and Graphene Oxide 0.5 g of graphene oxide was not in direct contact with hydrazinium carboxylate ($H_3N^+NHCO_2^-$), and about 0.2 g of hydrazinium carboxylate ($H_3N^+NHCO_2^-$) was placed on the bottom of a vessel and kept at 90° C. for 12 hours for reaction there between. Reduction was carried out using vapor gas generated at that time. The other details were the same as those of Example 1. The results of analysis were as shown in FIG. 10 to FIG. 12.

Results of Elemental Analysis:
1) Graphene oxide (GO): C, 54.86%; H, 2.17%; N, 0%
2) Reduced graphene oxide (RGO): C, 64.68%; H, 1.81%; N, 3.96%

Example 4

Figure 13:
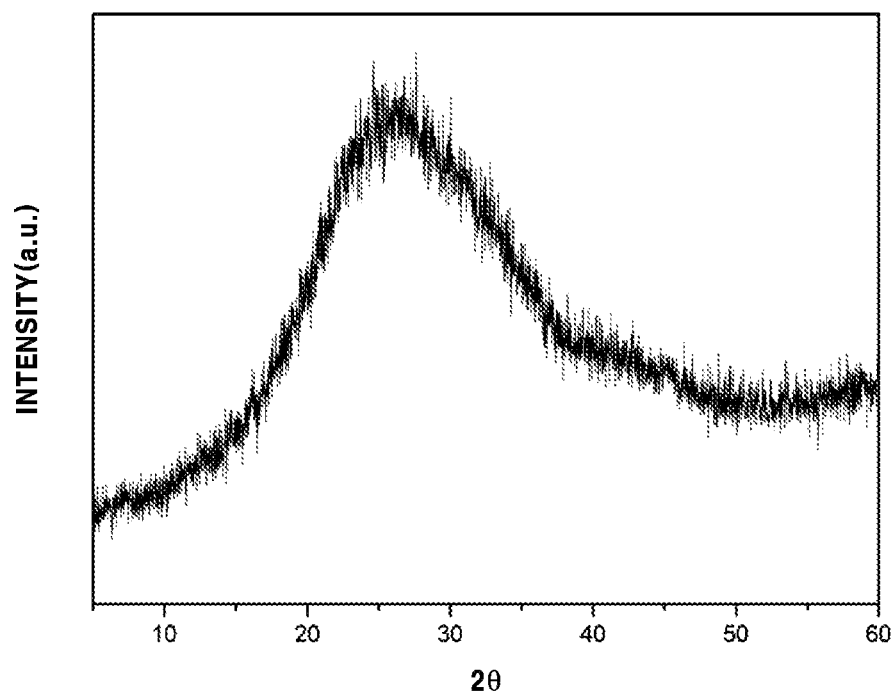
FIG. 13 shows an XRD spectrum of reduced graphene oxide in accordance with an example of the present disclosure.

Preparation of Reduced Graphene Oxide by Gas-Solid Reaction Between Hydrazinium Carboxylate as a Solid Hydrazine and Graphene Oxide on AAO (Aluminum Anodic Oxide) Disc A graphene oxide aqueous solution was prepared at a concentration of 0.2 mg/mL. Then, graphene oxide in 20 μL of the graphene oxide aqueous solution was fixed on an AAO (aluminum anodic oxide) disc (diameter: 13 mm, pore size: 0.2 μm) using a vacuum filter. The graphene oxide fixed on the AAO (aluminum anodic oxide) disc was not in a direct contact with hydrazinium carboxylate ($H_3N^+NHCO_2^-$), and about 0.2 g of hydrazinium carboxylate ($H_3N^+NHCO_2^-$) was placed on the bottom of a vessel and kept at 90° C. for 12 hours for a reaction there between. The reduction was carried out using vapor gas generated at that time. The other details were the same as those of Example 2. The result of XRD analysis was as shown in FIG. 13.

Comparative Example 1

Preparation of Reduced Graphene Oxide Using Hydrated Hydrazine 0.4 g of liquid hydrazine hydrate (60 wt. %) was used as a reducing agent instead of the solid hydrazine. The other details were the same as those of Example 1.

Results of Elemental Analysis:
1) Graphene oxide (GO): C, 54.86%; H, 2.17%; N, 0%
2) Reduced graphene oxide (RGO): C, 45.56%; H, 1.63%; N, 1.92%

Comparative Example 2

Preparation of Reduced Graphene Oxide Using a Hydrated Hydrazine 0.4 g of liquid hydrazine hydrate (60 wt. %) was used as a reducing agent. The other details were the same as those of Example 2. The result thereof was the same as the result of Comparative Example 1.

Results of Elemental Analysis:
1) Graphene oxide (GO): C, 54.86%; H, 2.17%; N, 0%
2) Reduced graphene oxide (RGO): C, 64.76%; H, 1.68%; N, 5.40%

Example 5

0.5 g of hydrazinium carboxylate was used as a reducing agent. The other details were the same as those of Example 2.

Results of Elemental Analysis:
1) Graphene oxide (GO): C, 54.86%; H, 2.17%; N, 0%
2) Reduced graphene oxide (RGO): C, 80.72%; H, 0.55%; N, 4.15%

Example 6

0.05 g of hydrazinium carboxylate was used as a reducing agent. The other details were the same as those of Example 2.

Results of Elemental Analysis:
1) Graphene oxide (GO): C, 54.86%; H, 2.17%; N, 0%
2) Reduced graphene oxide (RGO): C, 59.23%; H, 1.79%; N, 0.62%

Example 7

0.1 g of graphene oxide was used, and 0.5 g of hydrazinium carboxylate was used as a reducing agent. The other details were the same as those of Example 2.

Results of Elemental Analysis:
1) Graphene oxide (GO): C, 54.86%; H, 2.17%; N, 0%
2) Reduced graphene oxide (RGO): C, 75.85%; H, 0.85%; N, 1.77%

Example 8

50 mL of methanol solvent was used with stirring. The other details were the same as those of Example 1. After 12 hours, the solvent was removed by centrifugation, and the resulting product was dried in an oven, so that 0.5 g of reduced graphene oxide was obtained.

Results of Elemental Analysis:
1) Graphene oxide (GO): C, 54.86%; H, 2.17%; N, 0%
2) Reduced graphene oxide (RGO): C, 59.33%; H, 1.67%; N, 1.29%

Example 9

50 mL of a diethylether solvent was used with stirring. The other details were the same as those of Example 8. 0.5 g of reduced graphene oxide was obtained.

Results of Elemental Analysis:
1) Graphene oxide (GO): C, 54.86%; H, 2.17%; N, 0%
2) Reduced graphene oxide (RGO): C, 58.07%; H, 2.12%; N, 1.22%

Example 10

50 mL of toluene solvent was used with stirring. The other details were the same as those of Example 8. 0.5 g of reduced graphene oxide was obtained.

Results of Elemental Analysis:
1) Graphene oxide (GO): C, 54.86%; H, 2.17%; N, 0%
2) Reduced graphene oxide (RGO): C, 58.67%; H, 2.16%; N, 1.23%

Example 11

50 mL of water solvent was used with stirring. After centrifugation, the resulting product was washed three times with each of 30 mL of methanol, diethylether and pentane. The other details were the same as those of Example 8. 0.5 g of reduced graphene oxide was obtained.

Results of Elemental Analysis:
1) Graphene oxide (GO): C, 54.86%; H, 2.17%; N, 0%
2) Reduced graphene oxide (RGO): C, 75.85%; H, 0.85%; N, 1.77%

Example 12

A methanol (50 mL)/ether (50 mL) solvent was used with stirring. The other details were the same as those of Example 8. 0.5 g of reduced graphene oxide was obtained.

Results of Elemental Analysis:
1) Graphene oxide (GO): C, 54.86%; H, 2.17%; N, 0%
2) Reduced graphene oxide (RGO): C, 56.46%; H, 2.09%; N, 1.09%

Example 13

A methanol (50 mL)/toluene (50 mL) solvent was used with stirring. The other details were the same as those of Example 8. 0.5 g of reduced graphene oxide was obtained.

Results of Elemental Analysis:
1) Graphene oxide (GO): C, 54.86%; H, 2.17%; N, 0%
2) Reduced graphene oxide (RGO): C, 54.99%; H, 2.09%; N, 0.99%

Example 14

A gas having air of 1 atm was used in a pressured-vessel. The other details were the same as those of Example 2.

Results of Elemental Analysis:
1) Graphene oxide (GO): C, 54.86%; H, 2.17%; N, 0%
2) Reduced graphene oxide (RGO): C, 75.85%; H, 0.85%; N, 1.78%

Example 15

A gas having oxygen of 5 atm was used in a pressured-vessel. The other details were the same as those of Example 2.

Results of Elemental Analysis:
1) Graphene oxide (GO): C, 54.86%; H, 2.17%; N, 0%
2) Reduced graphene oxide (RGO): C, 75.85%; H, 0.85%; N, 1.77%

Example 16

A gas having hydrogen of 5 atm was used in a pressured-vessel. The other details were the same as those of Example 2.

Results of Elemental Analysis:
1) Graphene oxide (GO): C, 54.86%; H, 2.17%; N, 0%
2) Reduced graphene oxide (RGO): C, 75.85%; H, 0.85%; N, 1.77%

Example 17

Figure 14A:
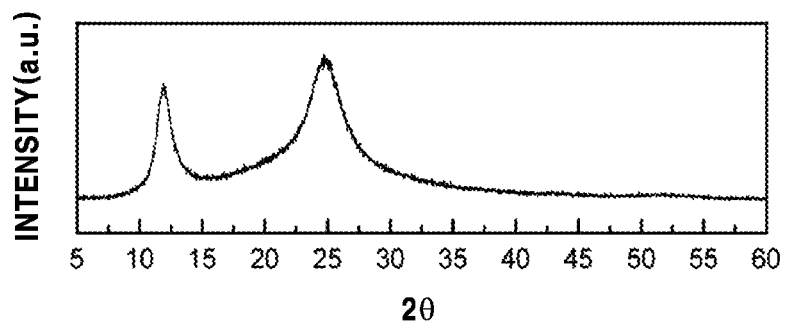
FIG. 14A shows an XRD spectrum of reduced graphene oxide prepared using 2-methyl hydrazinium carboxylate in accordance with an example of the present disclosure.

0.1 g of 2-methyl hydrazinium carboxylate ($(CH_3)H_2N^+NHCO_2^-$) was used as a reducing agent. The other details were the same as those of Example 3. The result of XRD analysis was as shown in FIG. 14A.

Results of Elemental Analysis:
1) Graphene oxide (GO): C, 54.86%; H, 2.17%; N, 0%
2) Reduced graphene oxide (RGO): C, 56.84%; H, 3.30%; N, 15.80%

Example 18

0.1 g of 2,2-dimethyl hydrazinium carboxylate ($(CH_3)_2HN^+NHCO_2^-$) was used as a reducing agent. The other details were the same as those of Example 3.

Results of Elemental Analysis:
1) Graphene oxide (GO): C, 54.86%; H, 2.17%; N, 0%
2) Reduced graphene oxide (RGO): C, 75.85%; H, 0.85%; N, 1.77%

Example 19

Figure 14B:
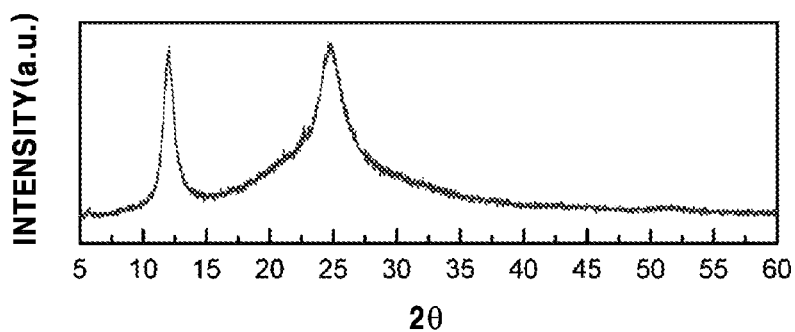
FIG. 14B shows an XRD spectrum of reduced graphene oxide prepared using dimethylammonium 2,2-dimethyl hydrazine carboxylate in accordance with an example of the present disclosure.

0.1 g of dimethylammonium 2,2-dimethylhydrazine carboxylate derived from 2,2-dimethyl hydrazinium carboxylate ($(CH_3)_2HN^+NHCO_2^-$) was used. The other details were the same as those of Example 3. The result of XRD analysis was as shown in FIG. 14B.

Results of Elemental Analysis:
1) Graphene oxide (GO): C, 54.86%; H, 2.17%; N, 0%
2) Reduced graphene oxide (RGO): C, 55.76%; H, 3.2507%; N, 7.85%

Example 20

Figure 14C:
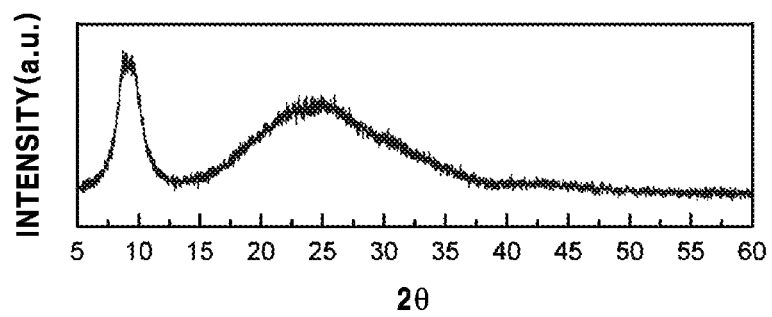
FIG. 14C shows an XRD spectrum of reduced graphene oxide prepared using 2-phenyl hydrazinium carboxylate in accordance with an example of the present disclosure.

0.1 g of 2-phenyl hydrazinium carboxylate ($H(CH_3)(C_6H_5)N^+NHCO_2^-$) was used. The other details were the same as those of Example 3. The result of XRD analysis was as shown in FIG. 14C.

Results of Elemental Analysis:
1) Graphene oxide (GO): C, 54.86%; H, 2.17%; N, 0%
2) Reduced graphene oxide (RGO): C, 54.42%; H, 2.28%; N, 3.55%

Example 21

Figure 14D:
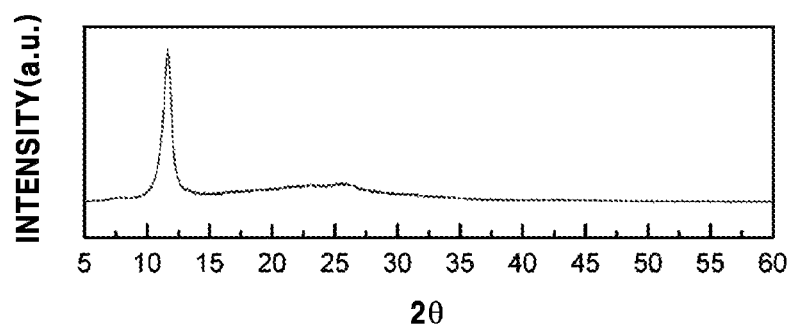
FIG. 14D shows an XRD spectrum of reduced graphene oxide prepared using 2-(pyridin-2-yl)hydrazinium carboxylate in accordance with an example of the present disclosure.

0.1 g of 2-(pyridin-2-yl)hydrazinium carboxylate ($H_2$(2-$C_5H_4N$)$N^+NHCO_2^-$) was used.
The other details were the same as those of Example 3. The result of XRD analysis was as shown in FIG. 14D.
Results of Elemental Analysis:
1) Graphene oxide (GO): C, 54.86%; H, 2.17%; N, 0%
2) Reduced graphene oxide (RGO): C, 51.41%; H, 2.16%; N, 3.56%

Example 22

Figure 14E:
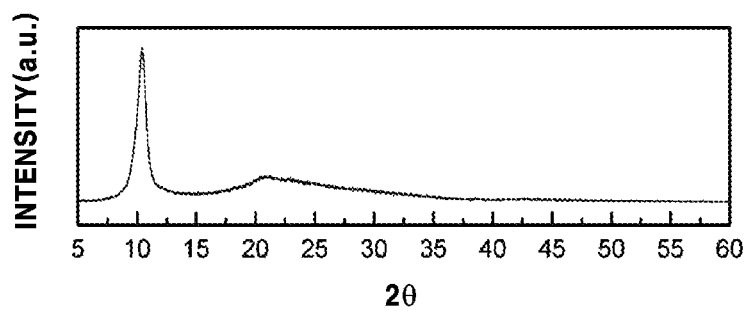
FIG. 14E shows an XRD spectrum of reduced graphene oxide prepared using 2-(2-hydroxyethyl)hydrazinium carboxylate in accordance with an example of the present disclosure

0.1 g of 2-(2-hydroxyethyl)hydrazinium carboxylate (($HOCH_2CH_2$)$H_2N^+NHCO_2^-$) was used. The other details were the same as those of Example 3. The result of XRD analysis was as shown in FIG. 14E.
Results of Elemental Analysis:
1) Graphene oxide (GO): C, 54.86%; H, 2.17%; N, 0%
2) Reduced graphene oxide (RGO): C, 47.51%; H, 2.49%; N, 3.70%

Example 23

0.1 g of 2-methyl-2-phenyl hydrazinium carboxylate (H($CH_3$)($C_6H_5$)$N^+NHCO_2^-$) was used. The other details were the same as those of Example 3.
Results of Elemental Analysis:
1) Graphene oxide (GO): C, 54.86%; H, 2.17%; N, 0%
2) Reduced graphene oxide (RGO): C, 75.85%; H, 0.85%; N, 1.77%

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

STATEMENT REGARDING THIRD PARTY RESEARCH PROJECT

This invention was made with Korean government support under Project No. 2012K001486 sponsored by the Ministry of Education and Science Technology and managed by Converging Research Headquarters for Frontier Medical Instruments (under Research Project Title: Converging Research Center Program; Subject Title: Development of Labeling Technologies for PET Radiopharmaceuticals; Research period: Jul. 1, 2009 through Jun. 30, 2014) with the beneficiary of sponsorship being Sogang University Research Foundation; and Korean government support under Project No. 201433014 sponsored by the Ministry of Science, ICT and Future Planning and managed by National Research Foundation of Korea (under Research Project Title: Korea CCS 2020 Project; Subject Title: Development of CO2 absorbents based on hydrazine; Research period: Jun. 1, 2014 through May 31, 2015) with the beneficiary of sponsorship being Sogang University Research Foundation.

We claim:

1. A method for preparing a reduced graphene oxide, comprising:
reducing a graphene oxide using, as a reducing agent, a solid hydrazine derivative compound represented by the following Chemical Formula II or Chemical Formula III that is generated from a reaction between a hydrazine represented by the following Chemical Formula I or its derivative with carbon dioxide:

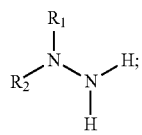
[Chemical Formula I]

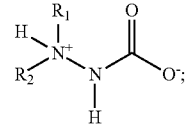
[Chemical Formula II]

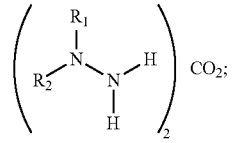
[Chemical Formula III]

wherein in Chemical Formulas I, II and III,
each of $R_1$ and $R_2$ is independently hydrogen; or, a member selected from the group consisting of an aliphatic hydrocarbon group of 1 to 30 carbons, a substitutable aliphatic hydrocarbon group of 1 to 30 carbons, a substitutable aliphatic cyclic group of 3 to 30 carbons, an aliphatic heterocyclic group of 3 to 30 carbons, an aromatic cyclic group of 6 to 30 carbons, and an aromatic heterocyclic group of 6 to 30 carbons; or, a member selected from the group consisting of an aliphatic hydrocarbon group of 1 to 30 carbons including at least one of Si, O, S, Se, N, P, or As, an aliphatic cyclic group of 3 to 30 carbons including at least one of Si, O, S, Se, N, P, or As, an aliphatic heterocyclic group of 3 to 30 carbons including at least one of Si, O, S, Se, N, P, or As, and an aromatic heterocyclic group of 6 to 30 carbons including at least one of Si, O, S, Se, N, P, or As.

2. The method for preparing reduced graphene oxide of claim 1,
wherein the reducing the graphene oxide is performed without using a solvent.

3. The method for preparing reduced graphene oxide of claim 2,
wherein the reducing the graphene oxide includes mixing the solid hydrazine derivative compound with the graphene oxide by grinding or milling those so as to be reacted in a solid state.

4. The method for preparing reduced graphene oxide of claim 3,
wherein the reducing the graphene oxide is performed at a temperature range of from room temperature to 80° C.

5. The method for preparing reduced graphene oxide of claim 3, wherein the reducing the graphene oxide is performed for 60 hours or less.

6. The method for preparing reduced graphene oxide of claim 2,
wherein the reducing the graphene oxide includes heating and sublimating the solid hydrazine derivative so as to be reacted with the graphene oxide.

7. The method for preparing reduced graphene oxide of claim 6,
wherein the graphene oxide is in a form of a film or thin film.

8. The method for preparing reduced graphene oxide of claim 6,
wherein the heating and sublimation is performed at a temperature range of 250° C. or less.

9. The method for preparing reduced graphene oxide of claim 1,
wherein the reducing the graphene oxide is performed by reacting the solid hydrazine derivative compound and the graphene oxide in a slurry state in the presence of a solvent including an aliphatic hydrocarbon group of 1 to 30 carbons, a substitutable aliphatic hydrocarbon group of 1 to 30 carbons, a substitutable aliphatic cyclic group of 3 to 30 carbons, an aliphatic heterocyclic group of 3 to 30 carbons, an aromatic cyclic group of 6 to 30 carbons, an aromatic heterocyclic group of 6 to 30 carbons, an aliphatic hydrocarbon group of 1 to 30 carbons including at least one of Si, O, S, Se, N, P or As, an aliphatic cyclic group of 3 to 30 carbons including at least one of Si, O, S, Se, N, P or As, an aliphatic heterocyclic group of 3 to 30 carbons including at least one of Si, O, S, Se, N, P or As, an aromatic heterocyclic group of 6 to 30 carbons including at least one of Si, O, S, Se, N, P or As, an alcohol of $C_1$-$C_{12}$, and an ether of $C_2$-$C_{12}$, or a mixed solvent thereof.

10. The method for preparing reduced graphene oxide of claim 9, further comprising:
removing the solvent by centrifugation after the reducing.

11. The method for preparing reduced graphene oxide of claim 1,
wherein a weight ratio of the solid hydrazine derivative with respect to the graphene oxide is 1:0.1 to 5.

12. The method for preparing reduced graphene oxide of claim 1,
wherein the reducing the graphene oxide is performed in a pressured-vessel using a gas having a pressure of from 0.1 atm to 500 atm.

13. The method for preparing reduced graphene oxide of claim 12,
wherein the gas includes a member selected from the group consisting of oxygen, nitrogen, argon, hydrogen, and combinations thereof.

* * * * *